United States Patent
Hirano et al.

(10) Patent No.: US 11,246,516 B2
(45) Date of Patent: Feb. 15, 2022

(54) MEASURING APPARATUS AND MEASURING METHOD

(71) Applicant: KYOCERA Corporation, Kyoto (JP)

(72) Inventors: Asao Hirano, Tokyo (JP); Tomoyuki Tougasaki, Sagamihara (JP); Takeshi Higuchi, Yokohama (JP)

(73) Assignee: KYOCERA Corporation, Kyoto (JP)

( * ) Notice: Subject to any disclaimer, the term of this patent is extended or adjusted under 35 U.S.C. 154(b) by 201 days.

(21) Appl. No.: 16/491,258

(22) PCT Filed: Feb. 19, 2018

(86) PCT No.: PCT/JP2018/005811
§ 371 (c)(1),
(2) Date: Sep. 5, 2019

(87) PCT Pub. No.: WO2018/163785
PCT Pub. Date: Sep. 13, 2018

(65) Prior Publication Data
US 2020/0029875 A1    Jan. 30, 2020

(30) Foreign Application Priority Data

Mar. 8, 2017 (JP) .............................. JP2017-044072
Aug. 24, 2017 (JP) .............................. JP2017-161530

(51) Int. Cl.
*A61B 5/1455* (2006.01)
*A61B 5/0205* (2006.01)
(Continued)

(52) U.S. Cl.
CPC ........ *A61B 5/14552* (2013.01); *A61B 5/0205* (2013.01); *A61B 5/0261* (2013.01); *A61B 5/7275* (2013.01); *A61B 2562/0238* (2013.01)

(58) Field of Classification Search
CPC . A61B 5/14552; A61B 5/0205; A61B 5/0261; A61B 5/7275; A61B 2562/0238; A61B 5/721; A61B 5/14551
See application file for complete search history.

(56) References Cited

U.S. PATENT DOCUMENTS 5,575,285 A     11/1996  Takanashi et al.
8,311,601 B2 *  11/2012  Besko ................ A61B 5/14552
                                                  600/323
(Continued)

FOREIGN PATENT DOCUMENTS

JP    H03-021208 Y2    5/1991
JP    H06-066633 U     9/1994
(Continued)

OTHER PUBLICATIONS

J H G M Klaessens et al.; "Monitoring cerebral perfusion using near-infrared spectroscopy and laser Doppler flowmetry"; Physiological Measurement; Institute of Physics Publishing; Nov. 3, 2003; pp. N35-N40; vol. 24, No. 4, XP020073656; ISSN: 0967-3334; DOI: 10.1088/0967-3334/24/4/N03.
(Continued)

*Primary Examiner* — Eric F Winakur
*Assistant Examiner* — Abid A Mustansir
(74) *Attorney, Agent, or Firm* — Studebaker & Brackett PC

(57) ABSTRACT

A measuring apparatus includes a first light source for emitting light of a first wavelength, a second light source for emitting laser light of a second wavelength different from the first wavelength, a first optical detector for receiving scattered laser light of the second wavelength from a measured part, a second optical detector for receiving transmitted light of the first wavelength from the measured part, a third optical detector for receiving transmitted laser light of the second wavelength from the measured part, and a
(Continued)

controller configured to measure a blood flow amount based on an output of the first optical detector and an oxygen saturation based on outputs of the second optical detector and the third optical detector.

7 Claims, 8 Drawing Sheets

(51) Int. Cl.
*A61B 5/026* (2006.01)
*A61B 5/00* (2006.01)

(56) References Cited

U.S. PATENT DOCUMENTS

| | | | |
|---|---|---|---|
| 2008/0171915 | A1 | 7/2008 | Kawajiri et al. |
| 2010/0056887 | A1 | 3/2010 | Kimura et al. |
| 2010/0240973 | A1 | 9/2010 | Presura et al. |
| 2011/0034789 | A1* | 2/2011 | Haisley .............. A61B 5/14551 600/324 |
| 2012/0209095 | A1* | 8/2012 | Huiku ................ A61B 5/14551 600/322 |
| 2017/0251962 | A1* | 9/2017 | Shiho .................... A61B 5/681 |
| 2017/0273575 | A1* | 9/2017 | Umekawa .............. A61B 5/725 |
| 2017/0325742 | A1* | 11/2017 | Prior .................... A61B 5/6826 |

FOREIGN PATENT DOCUMENTS

| | | |
|---|---|---|
| JP | H07-171140 A | 7/1995 |
| JP | 2003-508144 A | 3/2003 |
| JP | 2006-247133 A | 9/2006 |
| JP | 2008-532680 A | 8/2008 |
| WO | 01/17421 A1 | 3/2001 |
| WO | 2007/012931 A2 | 2/2007 |
| WO | 2008/065699 A1 | 6/2008 |

OTHER PUBLICATIONS

Yasuma, Fumihiko, "Periodic Breathing with Central Sleep Apena at High Altitude", Nippon Rinsho, vol. 66, Supll. 2, Apr. 30, 2008, pp. 245-248 (with English translation of the critical portions (p. 247, 2nd paragraph).

* cited by examiner

MEASURING APPARATUS AND MEASURING METHOD

CROSS-REFERENCE TO RELATED APPLICATION

This application claims priority to and the benefit of Japanese Patent Applications No. 2017-044072 (filed on Mar. 8, 2017) and No. 2017-161530 (filed on Aug. 24, 2017), the entire contents of which are incorporated herein by reference.

TECHNICAL FIELD

The present disclosure relates to a measuring apparatus and a measuring method.

BACKGROUND

Pulse oximeters for measuring arterial oxygen saturation are conventionally known (e.g., see PTL 1). Blood flow measuring apparatus that emit laser light to a fingertip and measure blood flow based on scattered light from the blood flow in fingertip capillaries are conventionally known (e.g., see PTL 2).

SUMMARY

A measuring apparatus according to an embodiment includes a first light source, a second light source, a first optical detector, a second optical detector, a third optical detector, and a controller. The first light source emits light of a first wavelength. The second light source emits laser light of a second wavelength different from the first wavelength. The first optical detector receives scattered light of laser light of the second wavelength from a measured part. The second optical detector receives transmitted light of the first wavelength from the measured part. The third optical detector receives transmitted laser light of the second wavelength from the measured part. The controller is configured to measure a blood flow amount based on an output of the first optical detector and an oxygen saturation based on outputs of the second optical detector and the third optical detector.

A measuring apparatus according to another embodiment includes a first light source, a second light source, a first optical detector, a second optical detector, and a controller. The first light source emits light of a first wavelength. The second light source emits laser light of a second wavelength different from the first wavelength. The first optical detector receives scattered laser light of the second wavelength from a measured part. The second optical detector receives transmitted light of the first wavelength and transmitted laser light of the second wavelength from the measured part. The controller is configured to measure a blood flow amount based on an output of the first optical detector and an oxygen saturation based on an output of the second optical detector.

A measuring apparatus according to another embodiment includes a first light source, a second light source, a first optical detector, a second optical detector, and a controller. The first light source emits light of a first wavelength. The second light source emits laser light of a second wavelength different from the first wavelength. The first optical detector receives scattered laser light of the first wavelength from a measured part. The second optical detector receives transmitted laser light of the second wavelength and scattered laser light of the first wavelength from the measured part. The controller measures a blood flow amount and an oxygen saturation based on outputs of the first optical detector and the second optical detector.

A measuring apparatus according to another embodiment includes a first light source, a second light source, an optical detector, and a controller. The first light source emits laser light of a first wavelength. The second light source emits laser light of a second wavelength different from the first wavelength. The optical detector receives transmitted laser light of the first wavelength and reflected laser light of the second wavelength from a measured part. The controller measures a blood flow amount and an oxygen saturation based on an output of the optical detector.

A measuring method according to an embodiment is a measuring method of a measuring apparatus. The measuring method includes a step of emitting light of a first wavelength to a measured part, and a step of emitting laser light of a second wavelength different from the first wavelength to the measured part. The measuring method also includes a step of receiving scattered laser light of the second wavelength from the measured part, a step of receiving transmitted light of the first wavelength from the measured part, and a step of receiving transmitted light of the second wavelength from the measured part. The measuring method further includes a step of measuring a blood flow amount based on scattered laser light of the second wavelength and a step of measuring an oxygen saturation based on transmitted light of the first wavelength and transmitted laser light of the second wavelength.

A measuring method according to another embodiment is a measuring method of a measuring apparatus. The measuring method includes a step of emitting laser light of a first wavelength to a measured part, and a step of emitting laser light of a second wavelength different from the first wavelength to the measured part. The measuring method also includes a step of receiving transmitted laser light or scattered laser light of the first wavelength from the measured part, and a step of receiving transmitted laser light or scattered laser light of the second wavelength from the measured part. The measuring method further includes a step of measuring an oxygen saturation based on transmitted laser light or scattered laser light of the first wavelength and transmitted laser light or scattered laser light of the second wavelength.

DETAILED DESCRIPTION

Hereinafter, embodiments of the present disclosure will be described in detail with reference to the accompanying drawings.

First Embodiment

Figure 1:
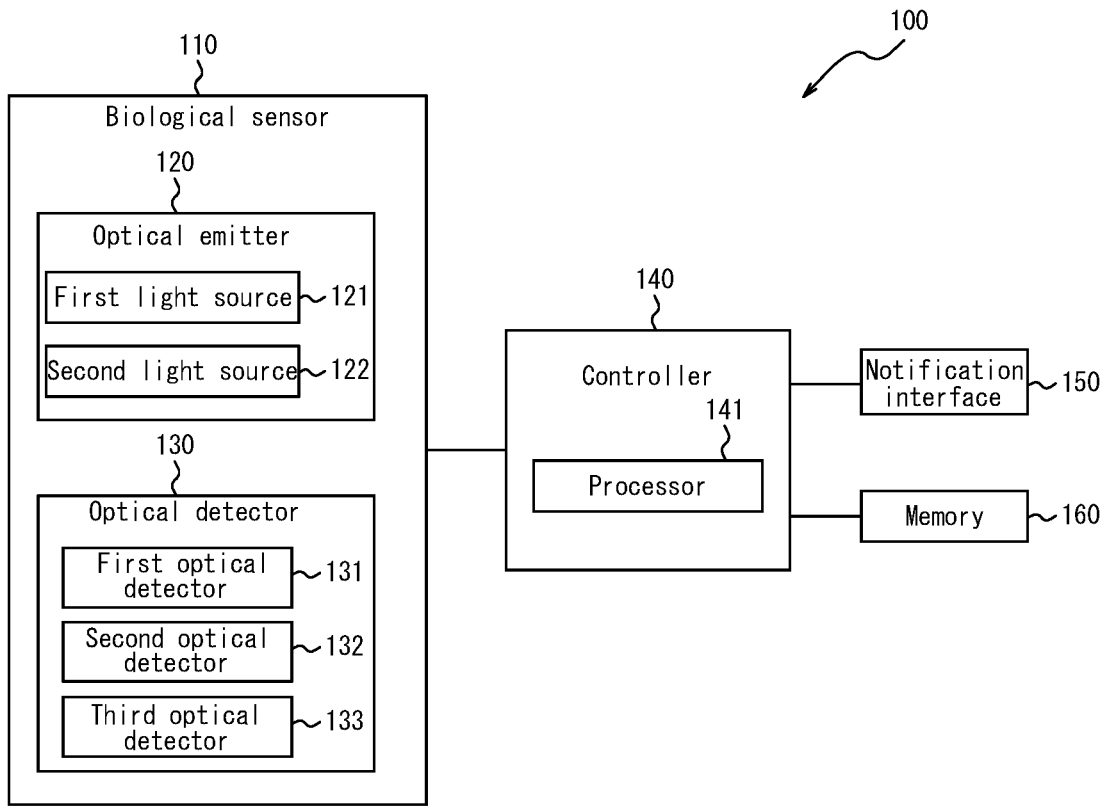
FIG. 1 is a functional block diagram illustrating a schematic configuration of a measuring apparatus according to a first embodiment.

FIG. 1 is a functional block diagram illustrating a schematic configuration of a measuring apparatus 100 according to a first embodiment. The measuring apparatus 100 according to the present embodiment includes a biological sensor 110, a controller 140, a notification interface 150, and a memory 160.

The measuring apparatus 100 acquires a biological measurement output of a subject (a user) in contact with the measuring apparatus 100 by using the biological sensor 110 and measures biological information based on the biological measurement outputs. The measuring apparatus 100 according to the present embodiment can measure oxygen saturation and a blood flow amount of the subject by using the biological sensor 110. The measuring apparatus 100 according to the present embodiment can measure, for example, percutaneous arterial oxygen saturation ($SpO_2$, S: Saturation, P: Percutaneous or Pulse Oximetry, $O_2$: Oxygen) as a value indicating the oxygen saturation of the subject. However, the biological information measured by the measuring apparatus 100 is not limited to $SpO_2$ and blood flow amount. The measuring apparatus 100 may measure any biological information that can be measured by the biological sensor 110. Hereinafter, $SpO_2$ will also be referred to simply as oxygen saturation. As a value indicating oxygen saturation, there also is $SaO_2$ (S: Saturation, a: artery, $O_2$: Oxygen), that indicates a measured value of oxygen saturation of arterial blood. $SpO_2$ is a method for indirectly measuring $SaO_2$ and, under prepared measurement conditions, both take an approximate value.

The biological sensor 110 acquires the biological measurement output of a measured part of the subject in contact with the measuring apparatus 100. The measured part is any part from which the biological measurement output can be acquired. According to the present embodiment, the measured part is assumed to be a finger in the description below. The measured part may be a wrist, an arm, an ear, a foot, or any other part or any combination thereof, in place of or in addition to a finger. The biological sensor 110 includes an optical emitter 120 and an optical detector 130. According to the present embodiment, the optical emitter 120 of the biological sensor 110 includes a first light source 121 and a second light source 122. According to the present embodiment, the optical detector 130 of the biological sensor 110 includes a first optical detector 131, a second optical detector 132, and a third optical detector 133.

Each of the first light source 121 and the second light source 122 emits light of a wavelength capable of detecting a predetermined component in the blood as measuring light.

The first light source 121 may be configured as, for example, an LED light source including an LED (Light Emitting Diode). The first light source 121 may be configured as, for example, an LD light source including an LD (Laser Diode). In the present embodiment, the first light source 121 will be described below as being configured as an LED light source.

The second light source 122 is configured as, for example, a laser light source including an LD. In the present embodiment, a VCSEL (vertical cavity surface emitting laser) diode is used as the laser light source. However, the laser light source may be another laser diode such as a DFB (Distributed Feedback) laser diode or an FP (Fabry-Perot) laser diode.

The first light source 121 and the second light source 122 emit light of different wavelengths. According to the present embodiment, the first light source 121 emits LED light of a first wavelength. When the first light source 121 is configured as the laser light source, the first light source 121 emits laser light of the first wavelength. The first wavelength is a wavelength that exhibits a large difference between absorbance in hemoglobin bonded with oxygen (hereinafter, referred to as "oxyhemoglobin") and absorbance in hemoglobin not bonded with oxygen (hereinafter, referred to as "reduced hemoglobin"). The first wavelength is, for example, 600 nm to 700 nm. The light emitted from the first light source 121 is so-called red light. In the present embodiment, the first wavelength will be assumed to be 660 nm in the following description. The second light source 122 emits laser light of a second wavelength (hereinafter, also referred to as "second laser light"). The second wavelength is different from the first wavelength. The second wavelength is a wavelength that exhibits a smaller difference between absorbance in oxyhemoglobin and absorbance in reduced hemoglobin than that of the first wavelength. The second wavelength is, for example, 800 nm to 1000 nm. The second laser light is so-called near infrared light. In the present embodiment, the second wavelength will be assumed to be 850 nm in the following description.

Each of the first optical detector 131, the second optical detector 132, and the third optical detector 133 is configured as, for example, a PD (Photo Diode).

The first optical detector 131 receives scattered light (detection light) of the measuring light (laser light) emitted to the measured part by the second light source 122 and scattered from the measured part as a biological measurement output. The second optical detector 132 receives transmitted light (detection light) of measuring light (LED light) emitted to the measured part by the first light source 121 and transmitted through the measured part as a biological measurement output. The third optical detector 133 receives transmitted light (detection light) of measuring light (laser light) emitted to the measured part by the second light source 122 and transmitted through the measured part as a biological measurement output. The biological sensor 110 transmits photoelectric conversion signals of the detection light received by the first optical detector 131, the second optical detector 132, and the third optical detector 133 to the controller 140.

Figure 2:
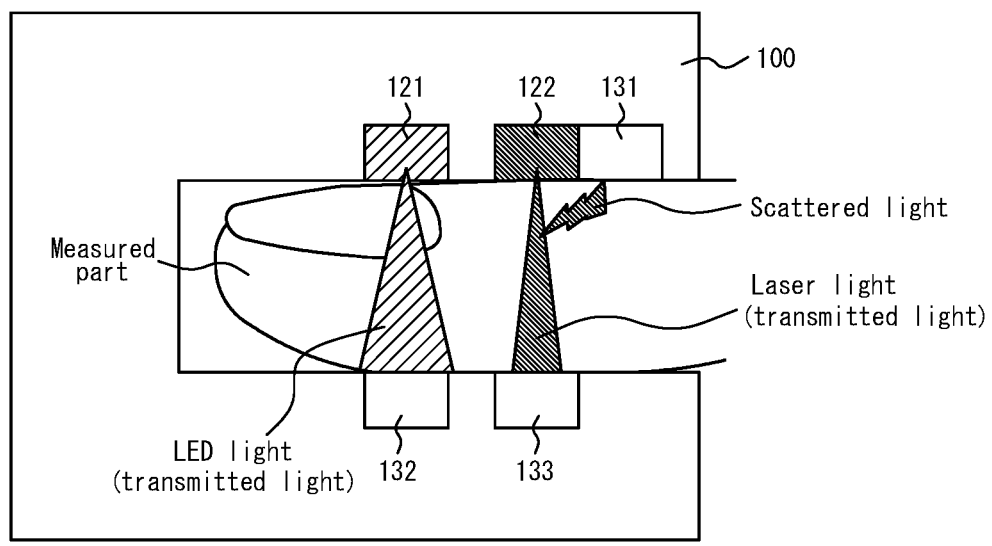
FIG. 2 is a schematic diagram illustrating an example of a usage state of the measuring apparatus of FIG. 1.

FIG. 2 is a schematic diagram illustrating an example of a usage state of the measuring apparatus 100. FIG. 2 illustrates an example of a cross-section of the measuring apparatus 100 and the measured part. In FIG. 2, the light sources of the optical emitter 120 and the optical detectors of the optical detector 130 alone are illustrated as functional units of the measuring apparatus 100. As schematically illustrated in FIG. 2, the measuring apparatus 100 measures the biological information in a state in which a subject causes the measured part to contact a specific location (a measuring unit) on the measuring apparatus 100. Although the measured part is a finger in FIG. 2, the measured part may be a wrist, an arm, an ear, a foot, or any other part. The measuring apparatus 100 may measure the biological information in a state in which the subject does not cause the measured part to contact the specific location (the measuring unit) of the measuring apparatus 100.

As schematically illustrated in FIG. 2, the first light source 121 and the second light source 122 are arranged in the measuring apparatus 100 to face the nail side of the finger at the time of measurement of the biological information.

The second optical detector 132 and the third optical detector 133 are arranged in the measuring apparatus 100 to oppose the first light source 121 and the second light source 122, respectively, across the finger serving as the measured part (i.e., on the pad side of the finger in the example of FIG. 2) at the time of measurement of the biological information. In this way, the second optical detector 132 and the third optical detector 133 can detect transmitted light from the first light source 121 and the second light source 122, respectively.

The first optical detector 131 is arranged in the measuring apparatus 100 at a position capable of receiving scattered light of laser light emitted to the measured part by the second light source 122 from the measured part. In an example illustrated in FIG. 2, the first optical detector 131 is arranged on the nail side of the finger, in a manner similar to the second light source 122.

As schematically illustrated in FIG. 2, the first optical detector 131 receives scattered light of laser light emitted by the second light source 122 from the measured part. The first optical detector 131 may be configured as a PD capable of detecting the light of a wavelength corresponding to scattered light of laser light (near infrared light).

As schematically illustrated in FIG. 2, the second optical detector 132 receives transmitted light of LED light emitted by the first light source 121 from the measured part. The second optical detector 132 may be configured as a PD capable of detecting the light of a wavelength corresponding to transmitted light of LED light (red light).

As schematically illustrated in FIG. 2, the third optical detector 133 receives transmitted light of laser light emitted by the second light source 122 from the measured part. The third optical detector 133 may be configured as a PD capable of detecting light of a wavelength corresponding to scattered light of laser light (near infrared light).

Referring back to FIG. 1, the controller 140 includes at least one processor 141 configured to control and manage the measuring apparatus 100 in its entirety including each functional block thereof. The controller 140 includes at least one processor 141 such as a CPU (Central Processing Unit) configured to execute a program defining a control procedure and thus realize its functionality. Such a program is stored in, for example, the memory 160 or an external storage medium connected to the measuring apparatus 100.

According to various embodiments, the at least one processor 141 may be configured as a single integrated circuit (IC), or a plurality of communicatively coupled integrated circuits IC and/or discrete circuits. The at least one processor 141 may be implemented according to various known technologies.

In one embodiment, the processor 141 includes, for example, one or more circuits or units configured to execute one or more data computing procedures or processes by executing instructions stored in an associated memory. In other embodiments, the processor 141 may be firmware (e.g., a discrete logic component) configured to execute one or more data computing procedures or processes.

According to various embodiments, the processor 141 may include one or more processors, controllers, microprocessors, microcontrollers, ASICs (application specific integrated circuits), digital signal processors, programmable logic devices, field programmable gate arrays, any combination these devices or their configurations, or any other known device or configuration combination, and perform the functions of the controller 140 described below.

The controller 140 calculates the blood flow amount in the measured part based on the output of the first optical detector (i.e., a photoelectric conversion signal of scattered light). Here, a blood flow measuring technology utilizing Doppler shift employed by the controller 140 will be described.

In the tissue of the living body, scattered light scattered by moving blood cells undergoes a frequency shift (a Doppler shift), due to the Doppler effect, that is proportional to the moving speed of the blood cells in the blood. The controller 140 detects a beat signal generated by light interference between scattered light from static tissues and scattered light from the moving blood cells. The beat signal represents intensity as a function of time. The controller 140 converts the beat signal into a power spectrum which represents power as a function of frequency. In the power spectrum of the beat signal, the Doppler shift frequency is proportional to the moving speed of the blood cells. In the power spectrum of the beat signal, the power corresponds to the amount of blood cells. The controller 140 acquires the blood flow amount by multiplying the power spectrum of the beat signal by the frequency and then integrating the multiplication result.

The controller 140 calculates $SpO_2$ of the measured part based on the outputs of the second optical detector 132 and the third optical detector 133 (i.e. the photoelectric conversion signals of transmitted light). Here, a measurement principle for $SpO_2$ employed by the controller 140 will be described.

In the blood, the reduced hemoglobin easily absorbs the light of the first wavelength, i.e., the red light, and has difficulty in absorbing the light of the second wavelength, i.e., the near infrared light. On the other hand, the oxygenated hemoglobin has difficulty in absorbing both the light of the first wavelength and the light of the second wavelength, i.e., the red light and the near infrared light. That is, the light of the first wavelength as the red light is easily absorbed by the reduced hemoglobin and hardly absorbed by the oxygenated hemoglobin. The light of the second wavelength as the near infrared light is hardly absorbed by the reduced hemoglobin and the oxygenated hemoglobin.

Thus, a ratio of the oxygenated hemoglobin to the reduced hemoglobin in the blood can be calculated based on a comparison between the intensity of the light received by the second optical detector 132 with respect to an amount of the light of the first wavelength (LED light according to the present embodiment) emitted by the first light source 121 and the intensity of the light received by the third optical detector 133 with respect to an amount of the light of the second wavelength (laser light according to the present embodiment) emitted by the second light source 122. The controller 140 can calculate $SpO_2$ based on the ratio of the oxygenated hemoglobin to the reduced hemoglobin. In particular, when $HbO_2$ represents an amount of oxygenated hemoglobin and Hb represents the reduced hemoglobin, $SpO_2$ is calculated from the following formula: $\{HbO_2/(Hb+HbO_2)\} \times 100$ (e.g., see PTL 1). The controller 140 calculates $SpO_2$ by using, for example, the formula.

Further, the controller 140 may estimate the likelihood that the subject gets altitude sickness (also called altitude impairment) based on the blood flow amount and the $SpO_2$ of the subject. Altitude sickness is more likely when $SpO_2$ decreases or when dehydrated. When the subject is dehydrated, insufficient moisture in the blood causes poor blood flow (decrease of the blood flow amount). Thus, the controller 140 can estimate the likelihood that the subject gets altitude sickness based on changes in the blood flow amount and $SpO_2$. The controller 140 may estimate the likelihood of altitude sickness by, for example, weighting the blood flow amount and $SpO_2$ using a predetermined algorithm. For example, the pulse oximeter disclosed in the PTL 1 can measure $SpO_2$ but cannot measure a blood flow amount. The measuring apparatus 100 according to the present embodiment can measure both $SpO_2$ and blood flow amount and thus is capable of estimating the likelihood of altitude sickness based on the two indexes, $SpO_2$ and the blood flow amount. Thus, the measuring apparatus 100 according to the present embodiment can more accurately estimate the likelihood of altitude sickness than an apparatus that estimates the likelihood of altitude sickness based on $SpO_2$ alone.

The notification interface 150 notifies information using a sound, a vibration, an image, or the like. The notification interface 150 may include a speaker, a vibrator, and a display device. The display device may be, for example, an LCD (Liquid Crystal Display), an OELD (Organic Electro-Luminescence Display), an IELD (Inorganic Electro-Luminescence Display), or the like. The notification interface 150 may notify, for example, a measurement result of $SpO_2$ and/or a blood flow amount. The notification interface 150 may notify, for example, information regarding a likelihood of altitude sickness.

The memory 160 may be configured as a semiconductor memory, a magnetic memory, or the like. The memory 160 stores various information and a program for operating the measuring apparatus 100. The memory 160 may also function as a working memory. The memory 160 may store, for example, $SpO_2$ and the blood flow amount of the subject calculated by the controller 140 as history information.

Figure 3:
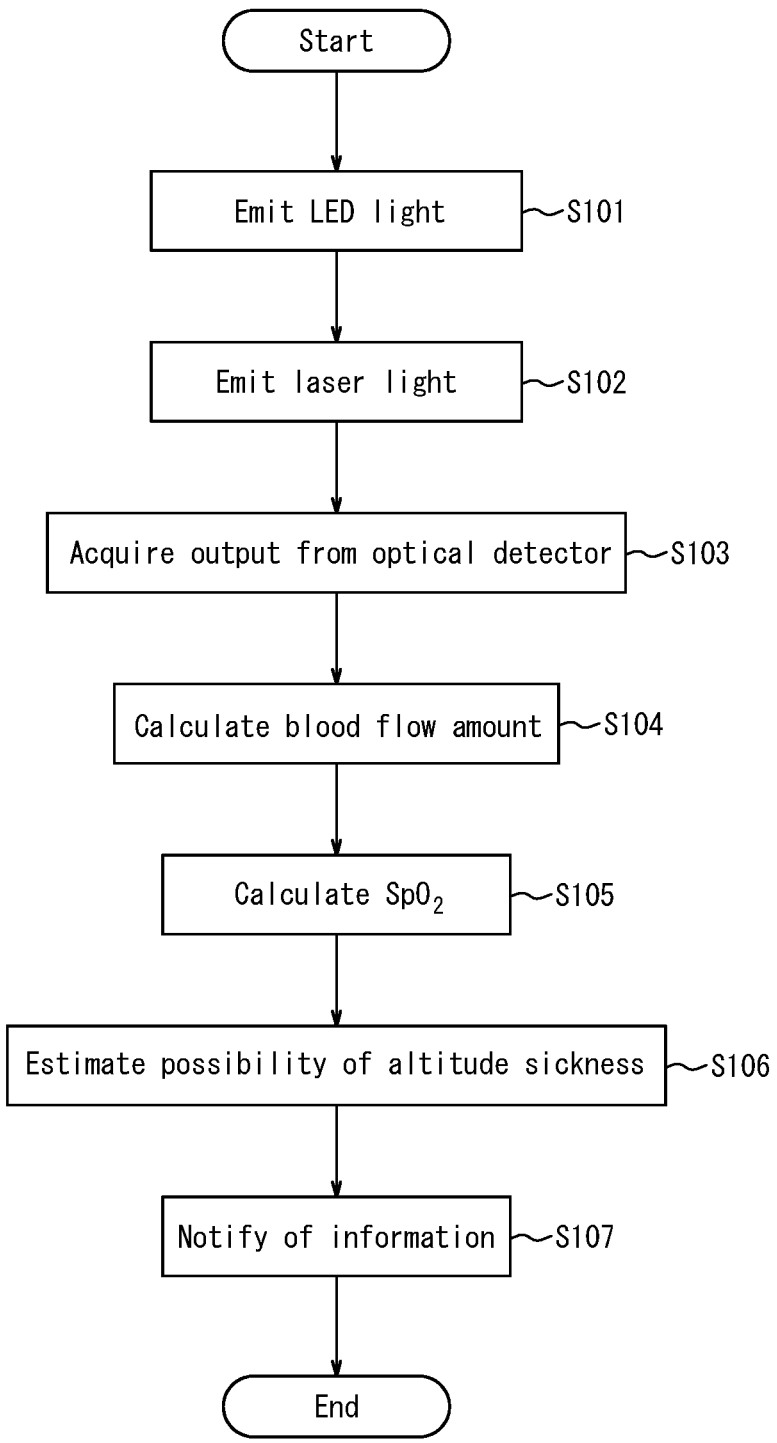
FIG. 3 is a flowchart illustrating an example of operations performed by a controller of FIG. 1.

Next, an example of operations performed by the controller 140 of the measuring apparatus 100 will be described with reference to the flowchart illustrated in FIG. 3. The controller 140 may repeat the flow illustrated in FIG. 3 when the measuring apparatus 100 is activated or when there is a predetermined input operation for starting the measuring operation. In a case in which the controller 140 has functionality which is able to detect whether the measured part is in contact with the measuring unit, the controller 140 may execute the flow illustrated in FIG. 3 when it is determined that the measured part is in contact with the measurement unit.

The controller 140 causes the first light source 121 to emit LED light (step S101).

The controller 140 causes the second light source 122 to emit laser light (step S102).

When the first light source 121 emits LED light and the second light source 122 emits laser light, the first optical detector 131, the second optical detector 132, and the third optical detector 133 receive the detection light from the measured part. That is, the first optical detector 131 receives scattered light of laser light, the second optical detector 132 receives transmitted light of LED light, and the third optical detector 133 receives transmitted light of laser light. The first optical detector 131, the second optical detector 132, and the third optical detector 133 transmit the photoelectric conversion signals of the detection light to the controller 140.

The controller 140 acquires the outputs from the first optical detector 131, the second optical detector 132, and the third optical detector 133 (step S103).

The controller 140 calculates the blood flow amount based on the output acquired from the first optical detector 131 (step S104).

The controller 140 calculates $SpO_2$ based on the outputs acquired from the second optical detector 132 and the third optical detector 133 (step S105).

The controller 140 estimates the likelihood that the subject gets altitude sickness based on the blood flow amount calculated in step S104 and $SpO_2$ calculated in step S105 (step S106).

The controller 140 causes the notification interface 150 to notify the blood flow amount, $SpO_2$, and the information regarding the likelihood of altitude sickness (step S107).

As described above, the measuring apparatus 100 according to the present embodiment measures the blood flow amount based on scattered light of laser light emitted by the second light source 122 and $SpO_2$ that is based on transmitted light of LED light emitted by the first light source 121 and transmitted light of laser light emitted by the second light source 122. The measuring apparatus 100 can measure both the blood flow amount and $SpO_2$ and thus improves usability for the user, as compared to a case in which the blood flow amount and $SpO_2$ are measured by individual apparatuses.

Laser light emitted by the second light source 122 is used for the measurement of both the blood flow amount and $SpO_2$. Thus, the measuring apparatus 100 according to the present embodiment can reduce the number of constituent elements thereof, as compared to a measuring apparatus provided with a light source for measuring the blood flow amount and a light source for measuring $SpO_2$. Accordingly, the measuring apparatus 100 according to the present embodiment can realize its downsizing. The downsizing of the apparatus makes it easier for the subject to carry it and thus improves usability.

Second Embodiment

Figure 4:
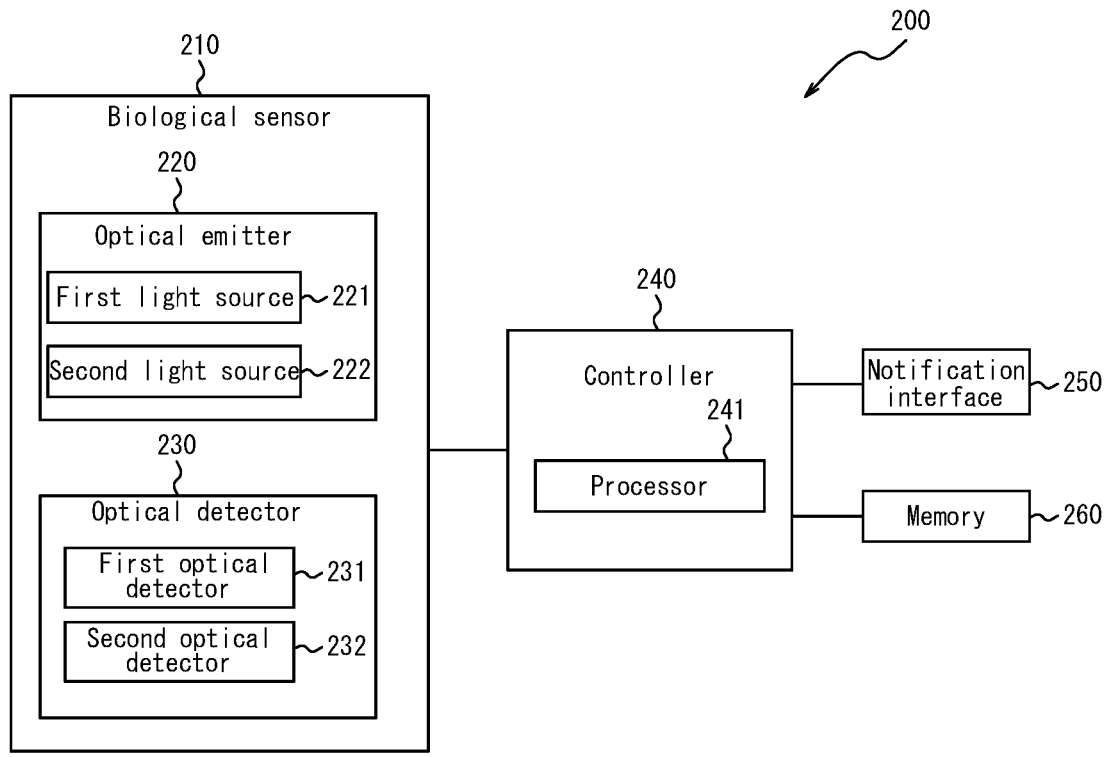
FIG. 4 is a functional block diagram illustrating a schematic configuration of a measuring apparatus according to a second embodiment.

FIG. 4 is a functional block diagram illustrating a schematic configuration of a measuring apparatus 200 according to a second embodiment. The measuring apparatus 200 according to the present embodiment includes a biological sensor 210, a controller 240, a notification interface 250, and a memory 260.

In the measuring apparatus 100 according to the first embodiment, the optical detector 130 includes three optical detectors: the first optical detector 131, the second optical detector 132, and the third optical detector 133. On the other hand, the measuring apparatus 200 according to the second embodiment includes two optical detectors: a first optical detector 231 and a second optical detector 232. The configuration of an optical emitter 220 of the measuring apparatus 200 according to the second embodiment may be similar to that of the optical emitter 120 of the measuring apparatus 100 according to the first embodiment.

According to the present embodiment, that is, the biological sensor 210 includes two light sources: a first light source 221 and a second light source 222, and two optical detectors: the first optical detector 231 and the second optical detector 232. The functions of the first light source 221 and the second light source 222 are similar to those of the first light source 121 and the second light source 122, respectively, of the first embodiment. That is, the first light source 221 emits LED light as the measuring light, and the second light source 222 emits laser light as the measuring light. In a manner similar to the first embodiment, the first light source 221 may emit laser light as the measuring light. The first light source 221 and the second light source 222 emit the measuring light at different timings. For example, the first light source 221 and the second light source 222 emit the measuring light alternately. That is, in a measuring operation of the measuring apparatus 200, LED light from the first light source 221 and laser light from the second light source 222 are alternately emitted to the measured part at, for example, predetermined intervals.

The functionality of the first optical detector 231 is similar to the function of the first optical detector 131 of the first embodiment. That is, the first optical detector 231 receives scattered light of laser light emitted by the second light source 222 from the measured part. The second optical detector 232 is configured as, for example, a so-called multi-frequency-responsive PD capable of detecting light of the wavelengths corresponding to both transmitted LED light (red light) and transmitted laser light (near infrared light) from the measured part. The second optical detector 232 detects transmitted LED light when LED light is emitted to the measured part by the first light source 221, and detects transmitted laser light when laser light is emitted to the measured part by the second light source 222. The biological sensor 210 transmits photoelectric conversion signals of the detection light received by the first optical detector 231 and the second optical detector 232 to the controller 240.

Figure 5:
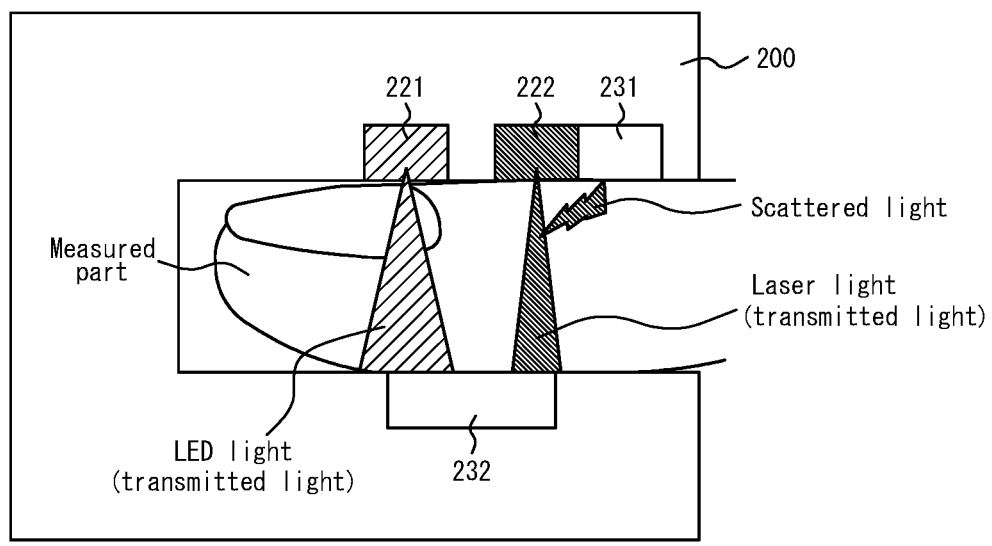
FIG. 5 is a schematic diagram illustrating an example of a usage state of the measuring apparatus of FIG. 4.

FIG. 5 is a schematic diagram illustrating an example of a usage state of the measuring apparatus 200. FIG. 5 is a diagram illustrating an example of a cross-section of the measuring apparatus 200 and the measured part. FIG. 5 illustrates the light sources of the optical emitter 220 and the optical detectors of the optical detector 230 alone as functional units of the measuring apparatus 200. As schematically illustrated in FIG. 5, the first optical detector 231 receives scattered light of laser light emitted by the second light source 222 from the measured part. The first optical detector 231 is arranged in a position of the measuring apparatus 200 capable of receiving scattered light of laser light emitted to the measured part by the second light source 222 from the measured part. In an example illustrated in FIG. 5, the first optical detector 231 is arranged to face the nail side of the finger in a manner similar to the second light source 222.

The second optical detector 232 receives transmitted light of LED light emitted by the first light source 221 and transmitted light of laser light emitted by the second light source 222 from the measured part. Because LED light and laser light are alternately emitted as described above, the second optical detector 232 alternately receives transmitted light of LED light and transmitted light of laser light. Although FIG. 5 illustrates both LED light and laser light, in reality either the first laser light or the second laser light is emitted to the measured part at a certain point in time, and the second optical detector 232 receives transmitted light of the emitted light. The second optical detector 232 is arranged at a position of the measuring apparatus 100 opposing the first light source 221 and the second light source 222 (i.e., on the pad side of the finger in the example of FIG. 5) across the finger serving as the measured part at the time of measurement of the biological information. In this way, the second optical detector 232 can detect transmitted light of the measuring light emitted by the first light source 221 and the second light source 222.

Referring back to FIG. 4, the controller 240 includes at least one processor 241 configured to control and manage the measuring apparatus 200 in its entirety including each functional block thereof. Functions of the controller 240 and the processor 241 are similar to those of the controller 140 and the processor 141, respectively, of the first embodiment. Thus, detailed descriptions will be omitted here. Also, functions of the notification interface 250 and the memory 260 are similar to those of the notification interface 150 and the memory 160, respectively, of the first embodiment. Thus, detailed descriptions will be omitted here.

In the measuring apparatus 200 according to the present embodiment, the controller 240 measures the blood flow amount and $SpO_2$ by performing operations similar to the operations described with reference to FIG. 3 and estimates the likelihood that the subject gets altitude sickness. In the present embodiment, the controller 240 acquires outputs from the first optical detector 231 and the second optical detector 232 in step S103. The controller 240 calculates the blood flow amount based on the output of the first optical detector 231 in step S104. The controller 240 calculates $SpO_2$ based on the outputs of the first optical detector 231 and the second optical detector 232 in step S105.

As described above, the measuring apparatus 200 according to the present embodiment can measure both the blood flow amount and $SpO_2$. Thus, usability for the subject is better than a case in which the blood flow amount and $SpO_2$ are measured by individual devices. The measuring apparatus 100 according to the present embodiment can receive transmitted light of LED light and transmitted light of laser light by the second optical detector 232 that corresponds to multiple frequencies. Thus, the biological sensor 210 and the measuring apparatus 200 may be downsized more than those of an apparatus in which transmitted light of LED light and transmitted light of laser light are received by two individual optical detectors. In this way, according to the measuring apparatus 200, usability is improved.

Third Embodiment

Figure 6:
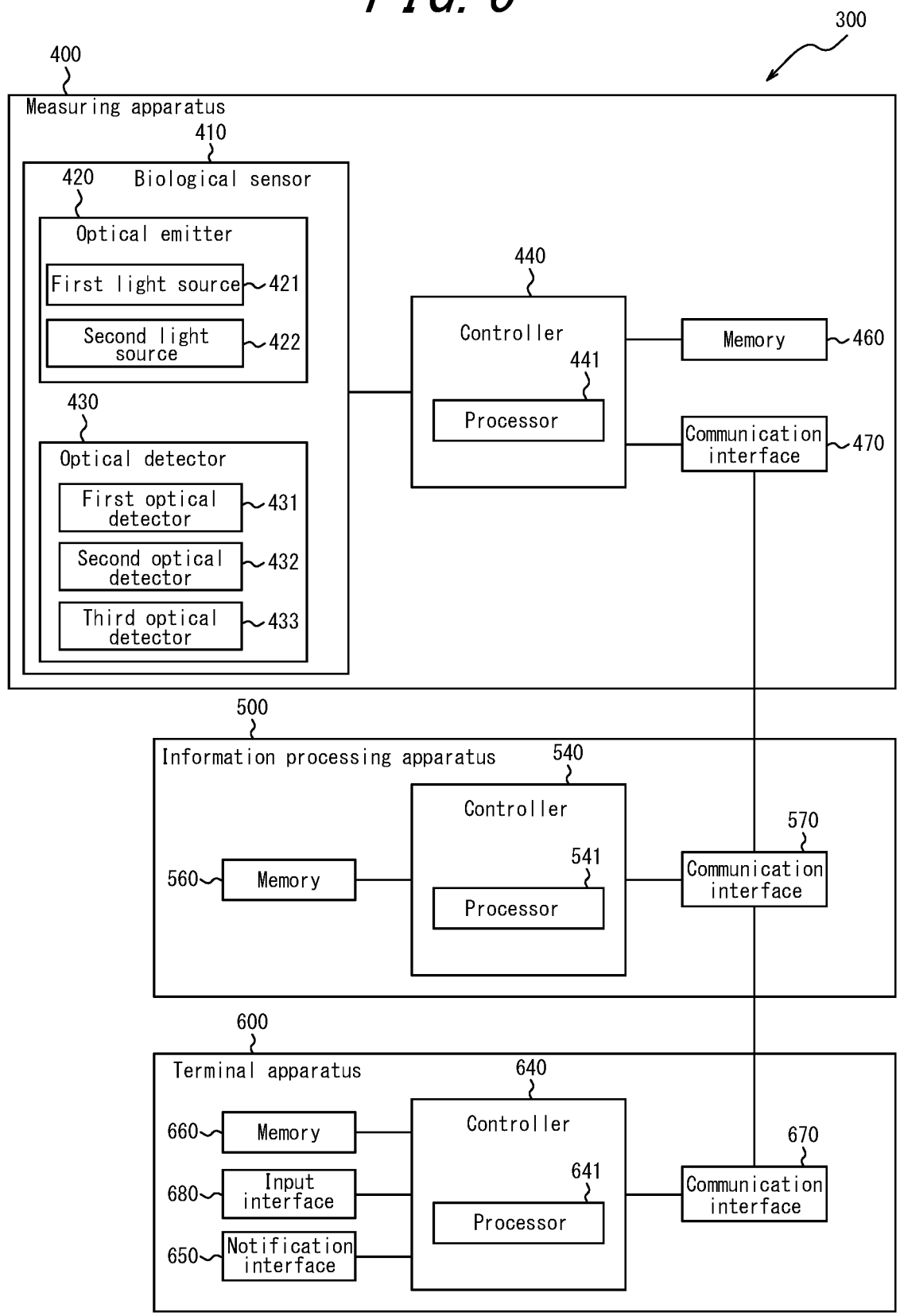
FIG. 6 is a functional block diagram illustrating a schematic configuration of a measuring system according to a third embodiment.

FIG. 6 is a functional block diagram illustrating a schematic configuration of a measuring system 300 according to a third embodiment. The measuring system 300 includes a measuring apparatus 400, an information processing apparatus 500, and a terminal apparatus 600. The information processing apparatus 500 is communicably connected to the measuring apparatus 400 and the terminal apparatus 600 via wired communication, wireless communication, or a combination thereof. The measuring apparatus 400 and the terminal apparatus 600 may directly communicate with each other. The network connecting the measuring apparatus 400, the information processing apparatus 500, and the terminal apparatus 600 together may be the Internet, a wireless LAN, or the like.

The measuring apparatus 400 is an apparatus configured to measure a biological measurement output by emitting measuring light to the measured part. The measuring apparatus 400 may transmit information regarding the biological measurement outputs to the information processing apparatus 500.

The information processing apparatus 500 may be configured as, for example, a server apparatus such as a computer. The information processing apparatus 500 may calculate the blood flow amount and $SpO_2$ of the subject based on the information regarding the biological measurement output acquired from the measuring apparatus 400. The information processing apparatus 500 may estimate the likelihood that the subject gets altitude sickness. The information processing apparatus 500 may store the calculation results of the blood flow amount and $SpO_2$ and information regarding the likelihood of altitude sickness. The information processing apparatus 500 may transmit the calculation results of the blood flow amount and $SpO_2$, and the information regarding the likelihood of altitude sickness, to the terminal apparatus 600.

The terminal apparatus 600 may be configured as, for example, a personal computer, a smartphone, a tablet computer, or the like. The terminal apparatus 600 may be owned by the subject. The terminal apparatus 600 may perform notification based on the calculation results of the blood flow amount and $SpO_2$ and the information regarding the likelihood of altitude sickness acquired from the information processing apparatus 500.

The measuring apparatus 400 includes a biological sensor 410, a controller 440, a notification interface 450, and a memory 460. The biological sensor 410 includes an optical emitter 420 and an optical detector 430. Configurations and functions of the optical emitter 420 and the optical detector 430 are similar to the optical emitter 120 and the optical detector 130, respectively, of the first embodiment. That is, the optical emitter 420 includes a first light source 421 for emitting LED light and a second light source 422 for emitting laser light. The optical detector 430 includes a first optical detector 431 configured to receive scattered light of laser light emitted by the second light source 422, a second optical detector 432 configured to receive transmitted light of LED light emitted by the first light source 421, and a third optical detector 433 configured to receive transmitted light of laser light emitted by the second light source 422. The measuring apparatus 400 according to the present embodiment can acquire biological measurement outputs in a manner similar to the measuring apparatus 100 of the first embodiment.

The controller 440 includes at least one processor 441 configured to control and manage the measuring apparatus 400 in its entirety, including each functional block thereof. The controller 440 includes at least one processor 441 such as a CPU configured to execute a program defining a control procedure and thus realize its functionality. Such a program is stored in, for example, the memory 460 or an external storage medium connected to the measuring apparatus 400. The processor 441 may have a configuration similar to, for example, the configuration of the processor 141 of the first embodiment. Thus, detailed descriptions will be omitted here. The controller 440 causes the biological sensor 410 to acquire the biological measurement outputs and transmits information regarding the biological measurement outputs to the information processing apparatus 500 via the communication interface 470.

The memory 460 may be configured as a semiconductor memory, a magnetic memory, or the like. The memory 460 stores various information and/or a program for operating the measuring apparatus 400. The memory 460 may also function as a working memory. The memory 460 may store, for example, data for the information regarding the biological measurement outputs (i.e., intensities of received detection light) acquired by the biological sensor 410.

The communication interface 470 transmits and receives various information by performing wired communication, wireless communication, or a combination thereof with the information processing apparatus 500. For example, the communication interface 570 transmits information regarding the biological measurement output measured by the measuring apparatus 400 to the information processing apparatus 500.

The information processing apparatus 500 includes a controller 540, a memory 560, and a communication interface 570.

The controller 540 includes at least one processor 541 configured to control and manage the information processing apparatus 500 in its entirety including each functional block thereof. The controller 540 includes at least one processor 541 such as a CPU configured to execute a program defining a control procedure and thus realize its functionality. Such a program is stored in, for example, the memory 560 or an external storage medium connected to the information processing apparatus 500. The processor 541 may have a configuration similar to, for example, the configuration of the processor 141 of the first embodiment. Thus, detailed descriptions will be omitted here. The controller 540 may calculate the blood flow amount and $SpO_2$ of the subject based on the information regarding the biological measurement outputs acquired from the measuring apparatus 400. The controller 540 may estimate the likelihood that the subject gets altitude sickness. The calculation method of the blood flow amount and $SpO_2$ and the estimation method of the likelihood of altitude sickness are similar to those described in the first embodiment. Thus, detailed descriptions will be omitted.

The memory 560 may be configured as a semiconductor memory, a magnetic memory, or the like. The memory 560 stores various information and/or a program for operating the information processing apparatus 500. The memory 560 may also function as a working memory. The memory 560 may store, for example, information regarding the biological measurement outputs acquired from the measuring apparatus 400. The memory 160 may store, for example, the blood flow amount and $SpO_2$ calculated by the controller 540 as well as various information used for the estimation of the likelihood of altitude sickness.

The communication interface 570 transmits and receives various information by performing wired communication, wireless communication, or a combination thereof with the measuring apparatus 400 and the terminal apparatus 600. For example, the communication interface 570 receives the information regarding the biological measurement outputs from the measuring apparatus 400. For example, the communication interface 570 transmits the blood flow amount and $SpO_2$ calculated by the information processing apparatus 500 and the information regarding the likelihood of altitude sickness to the terminal apparatus 600.

The terminal apparatus 600 includes a controller 640, a notification interface 650, a memory 660, a communication interface 670, and an input interface 680.

The controller 640 includes at least one processor 641 configured to control and manage the terminal apparatus 600 in its entirety, including each functional block thereof. The controller 640 includes at least one processor 641 such as a CPU configured to execute a program defining a control procedure and thus realize its functionality. Such a program is stored in, for example, a memory 660 or an external storage medium connected to the terminal apparatus 600. The processor 641 may have a configuration similar to, for example, the configuration of the processor 141 of the first embodiment. Thus, detailed descriptions will be omitted here. The controller 640 may cause the notification interface 650 to notify of the blood flow amount and $SpO_2$ acquired from the information processing apparatus 500 together with the information regarding the likelihood of altitude sickness.

The notification interface 650 notifies the information using a sound, a vibration, an image, or the like. The functions and the configuration of the notification interface 650 are similar to those of the notification interface 150 described in the first embodiment. Thus, detailed descriptions will be omitted here.

The memory 660 may be configured as a semiconductor memory, a magnetic memory, or the like. The memory 660 stores various information and/or a program for operating the terminal apparatus 600. The memory 660 may also function as a working memory. The memory 660 may store, for example, the blood flow amount and $SpO_2$ acquired from the information processing apparatus 500 as well as the information regarding the likelihood of altitude sickness.

The communication interface 670 transmits and receives various information performing wired communication, wireless communication, or a combination thereof with the information processing apparatus 500. For example, the communication interface 670 receives the blood flow amount and $SpO_2$ acquired from the information processing apparatus 500 and the information regarding the likelihood of altitude sickness from the information processing apparatus 500.

The input interface 680 is configured to receive an input operation from a user (e.g., the subject) of the terminal apparatus 600 and configured as, for example, an operation button (an operation key). The input interface 680 may be configured as a touch panel configured to display an operation key for receiving an input operation from the user in a portion of the display device and may receive a touch input operation made by the user.

Figure 7:
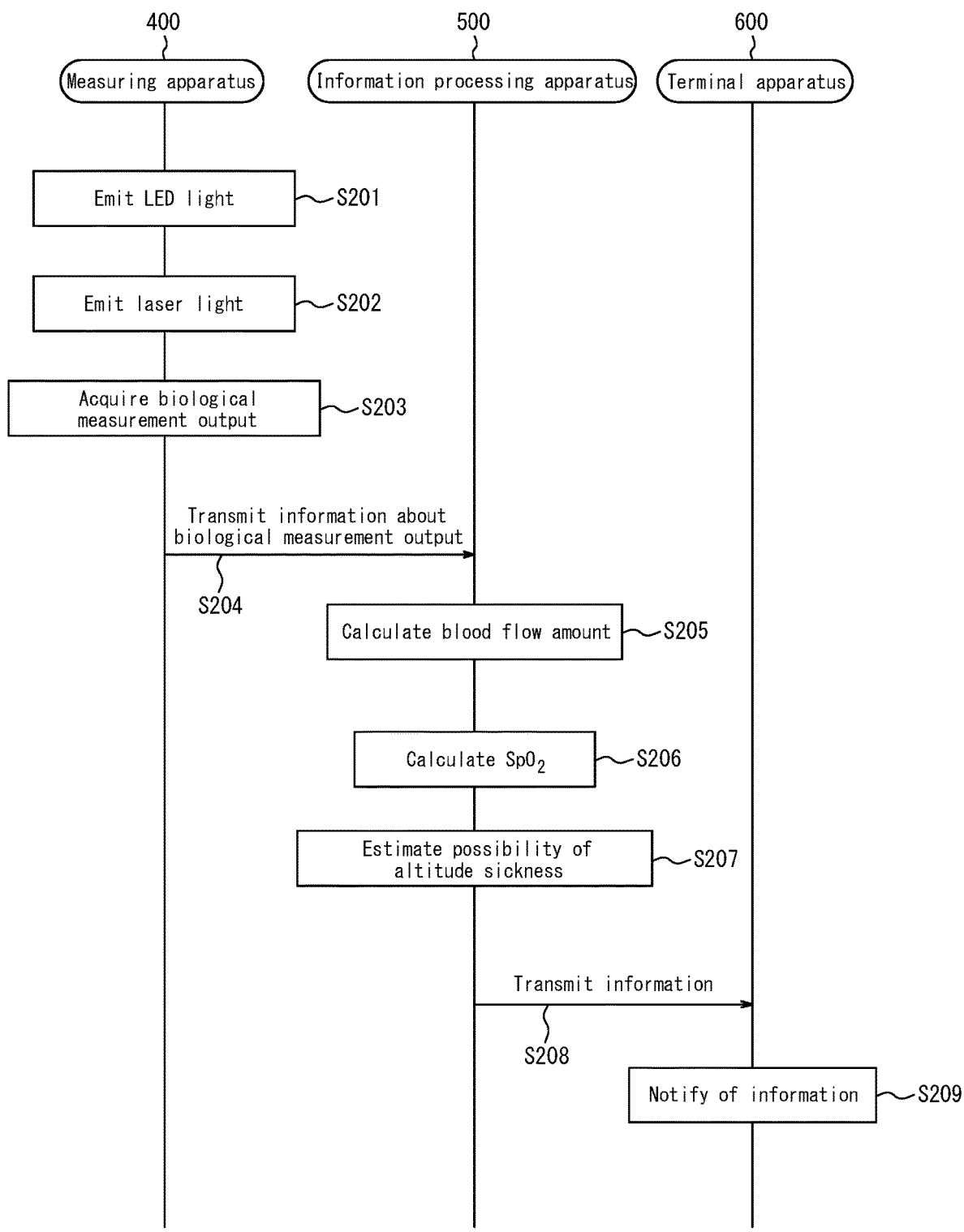
FIG. 7 is a sequence diagram illustrating an example of a control procedure of the measuring system of FIG. 6.

FIG. 7 is a sequence diagram illustrating an example of a control procedure performed by the measuring system 300. The procedure illustrated in FIG. 7 is executed when, for example, the measuring apparatus 400 is activated or a predetermined input operation for starting the measuring operation is performed. In a case in which the controller 440 of the measuring apparatus 400 has functionality which is able to detect whether the measured part is in contact with the measuring unit, the procedure illustrated in FIG. 7 may be executed when it is determined that the measured part is in contact with the measuring unit.

The measuring apparatus 400 causes the first light source 421 to emit LED light (step S201).

The measuring apparatus 400 causes the second light source 422 to emit laser light (step S202).

The measuring apparatus 400 acquires the output from the first optical detector 431, the second optical detector 432, and the third optical detector 433 (step S203).

The measuring apparatus 400 transmits the information regarding the biological measurement outputs to the information processing apparatus 500 via the communication interface 470 (step S204).

Upon receiving the information regarding the biological measurement output from the measuring apparatus 400, the information processing apparatus 500 calculates the blood flow amount based on the output of the first optical detector 431 (step S205).

The information processing apparatus 500 calculates $SpO_2$ based on the outputs of the second optical detector 432 and the third optical detector 433 (step S206).

The information processing apparatus 500 estimates the likelihood that the subject gets altitude sickness based on the blood flow amount calculated in step S205 and $SpO_2$ calculated in step S206 (step S207).

The information processing apparatus 500 transmits the blood flow amount, $SpO_2$, and the information regarding the likelihood of altitude sickness to the terminal apparatus 600 via the communication interface 570 (step S208).

Upon receiving the blood flow amount, $SpO_2$, and the information regarding the likelihood of altitude sickness from the information processing apparatus 500, the terminal apparatus 600 causes the notification interface 650 to notify of the blood flow amount, $SpO_2$, and the information regarding the likelihood of altitude sickness (step S209).

According to the present embodiment, the biological sensor 410 of the measuring apparatus 400 has been described as having a configuration similar to that of the biological sensor 110 of the first embodiment. However, the biological sensor 410 may have a configuration similar to that of the biological sensor 210 of the second embodiment.

In the present embodiment, the information processing apparatus 500 has been described as calculating the blood flow amount and $SpO_2$ and estimating the likelihood of altitude sickness. However, for example, the measuring apparatus 400 may perform the calculation of the blood flow amount and $SpO_2$ and the estimation of the likelihood of altitude sickness. In this case, the measuring apparatus 400 may transmit the calculation results of the blood flow amount and $SpO_2$ and the estimation result of the likelihood of altitude sickness to the information processing apparatus 500. The measuring system 300 does not need to include the information processing apparatus 500. In this case, the measuring apparatus 400 may transmit the calculation results of the blood flow amount and $SpO_2$ and the estimation result of the likelihood of altitude sickness to the terminal apparatus 600.

As described above, in the measuring system 300 according to the present embodiment, the measuring apparatus 400 acquires the biological measurement outputs and calculates the blood flow amount and $SpO_2$ based on the biological measurement outputs. Thus, the measuring system 300 according to the present embodiment does not need to use individual apparatuses for measuring the blood flow amount and $SpO_2$, and thus improves usability for the subject.

Laser light emitted by the second light source 422 of the measuring apparatus 400 of the measuring system 300 is used for the measurement of both the blood flow amount and $SpO_2$. Thus, the measuring apparatus 400 can reduce the number of constituent elements thereof, as compared with the measuring apparatus 400 that includes individual light sources used for measuring the blood flow amount and for measuring $SpO_2$. Accordingly, the apparatus can be downsized, and usability is improved.

Fourth Embodiment

Figure 8:
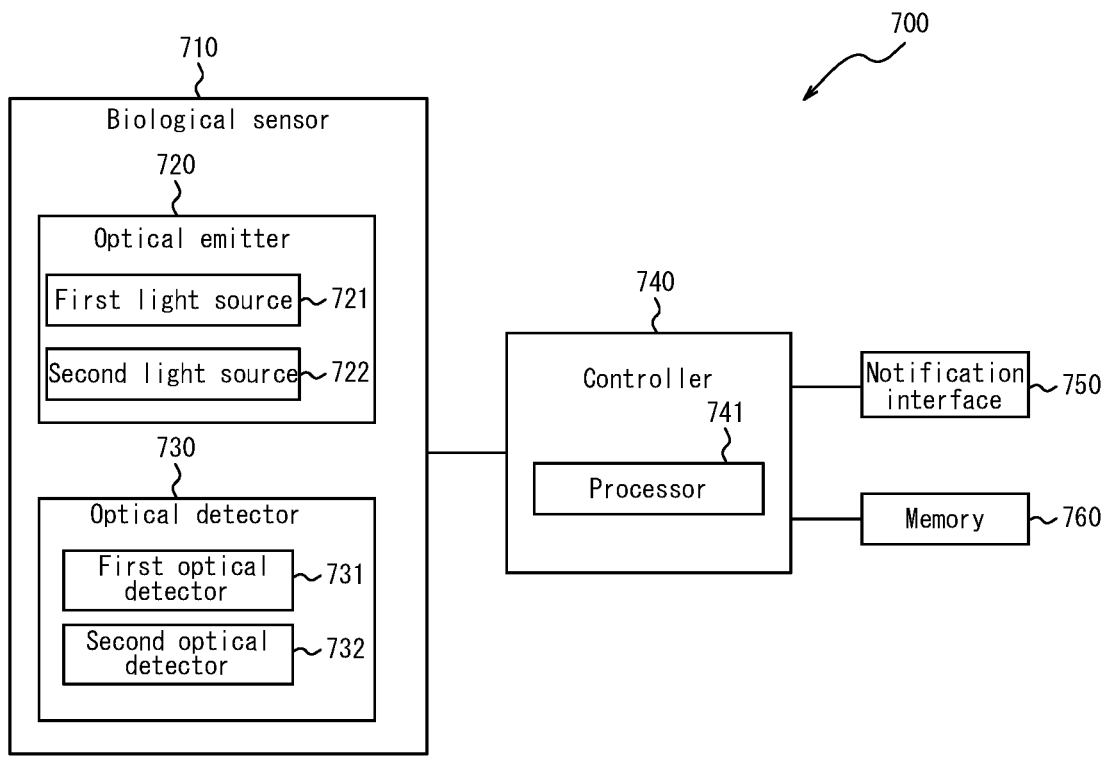
FIG. 8 is a functional block diagram illustrating a schematic configuration of a measuring apparatus according to a fourth embodiment.

FIG. 8 is a functional block diagram illustrating a schematic configuration of a measuring apparatus 700 according to a fourth embodiment. The measuring apparatus 700 according to the present embodiment includes a biological sensor 710, a controller 740, a notification interface 750, and a memory 760. The biological sensor 710 includes an optical emitter 720 and an optical detector 730.

The optical emitter 720 includes a first light source 721 and a second light source 722. According to the present embodiment, both the first light source 721 and the second light source 722 are configured as a laser light source by using, for example, the LDs. According to the present embodiment, that is, each of the first light source 721 and the second light source 722 emits laser light as the measuring light. The wavelengths of laser light emitted by the first light source 721 and the second light source 722 may correspond to the first wavelength and the second wavelength, respectively, described in the first embodiment. According to the present embodiment, that is, the first light source 72 emits laser light in a wavelength of, for example, 660 nm and the second light source 722 emits laser light in a wavelength of, for example, 850 nm.

The optical detector 730 includes a first optical detector 731 and a second optical detector 732. According to the present embodiment, the first optical detector 731 receives, for example, transmitted light of laser light (red light) emitted by the first light source 721 from the measured part. According to the present embodiment, the second optical detector 732 receives, for example, transmitted light of laser light (near infrared light) emitted by the second light source 722 from the measured part. The biological sensor 710 transmits photoelectric conversion signals of the detection light received by the first optical detector 731 and the second optical detector 732 to the controller 740.

Figure 9:
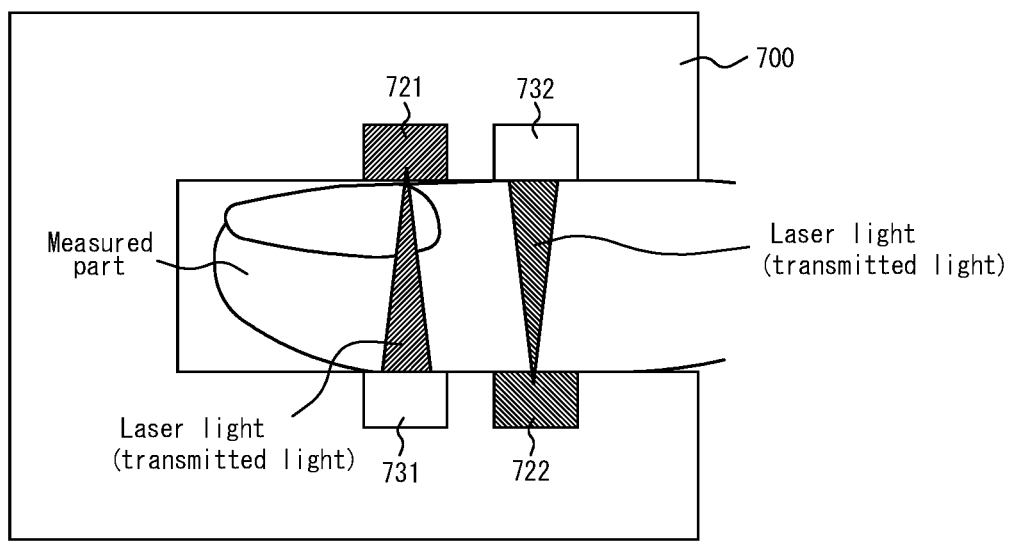
FIG. 9 is a schematic diagram illustrating an example of a using state of the measuring apparatus of FIG. 8.

FIG. 9 is a schematic diagram illustrating an example of a using state of the measuring apparatus 700. FIG. 9 is a diagram illustrating an example of a cross-section of the measuring apparatus 700 and the measured part. FIG. 9 illustrates the light sources of the optical emitter 720 and optical detectors of the optical detector 730 alone as the functional units of the measuring apparatus 700.

The first optical detector 731 is arranged at a position of the measuring apparatus 700 opposing the first light source 721 across the finger serving as the measured part at the time of measurement of the biological information. The second optical detector 732 is arranged at a position of the measuring apparatus 700 opposing the second light source 722 across the finger serving as the measured part at the time of measurement of the biological information. For example, when the first light source 721 is arranged to face the nail side of the finger as illustrated in FIG. 9, the first optical detector 731 is arranged to face the pad side of the finger. For example, when the second light source 722 is arranged to face the pad side of the finger as illustrated in FIG. 9, the second optical detector 732 is arranged to face the nail side of the finger. Note that FIG. 9 illustrates the arrangement by way of example only. For example, both the first light source 721 and the second light source 722 may be arranged on the nail side of the finger. In this case, both the first optical detector 731 and the second optical detector 732 are arranged to face the pad side of the finer. For example, both the first optical detector 731 and the second optical detector 732 may be arranged to face the pad side of the finer. In this case, both the first optical detector 731 and the second optical detector 732 are arranged to face the nail side of the finer. In this way, the first optical detector 731 and the second optical detector 732 can detect transmitted light of the measuring light emitted by the first light source 721 and the second light source 722, respectively.

Referring back to FIG. 8, the controller 740 includes at least one processor 741 configured to control and manage the measuring apparatus 700 in its entirety including each functional block thereof. The functions of the controller 740 and the processor 741 may be similar to those of the controller 140 and the processor 141, respectively, of the first embodiment.

According to the present embodiment, the controller 740 calculates SpO$_2$ of the measured part based on the outputs of the first optical detector 731 and the second optical detector 732 (i.e., the photoelectric conversion signals of transmitted light). The calculation method of SpO$_2$ may be similar to that described in the first embodiment. That is, the controller 740 calculates the ratio of the oxyhemoglobin to the reduced hemoglobin in the blood based on the intensity of the light received by the first optical detector 731 with respect to an amount of the light of the first wavelength emitted by the first light source 721 and the intensity of the light received by the second optical detector 732 with respect to an amount of the light of the second wavelength emitted by the second light source 722. Then, the controller 740 calculates SpO$_2$ by using the following formula: $\{HbO_2/(Hb+HbO_2)\} \times 100$ based on the ratio of the oxyhemoglobin to the reduced hemoglobin. In the formula, for example, HbO$_2$ may be calculated based on the intensity of transmitted light received by the first optical detector 731 after a portion of the measuring light is absorbed by the reduced hemoglobin. In the formula, for example, Hb+HbO$_2$ may be calculated based on the intensity of transmitted light received by the second optical detector 732 that is not absorbed by any one of the oxyhemoglobin and the reduced hemoglobin.

The functions of the notification interface 750 and the memory 760 are similar to those of the notification interface 150 and the memory 160, respectively, of the first embodiment. Thus, detailed descriptions will be omitted here.

As described above, the measuring apparatus 700 having the configuration in which both the first light source 721 and the second light source 722 emit laser light can calculate SpO$_2$. When both the first light source 721 and the second light source 722 of the measuring apparatus 700 emit laser light, the controller 740 does not perform step S101 for emitting LED light in the flow illustrated in FIG. 3. For example, the controller 740 may cause both the first light source 721 and the second light source 722 to emit laser light in step S102.

According to the fourth embodiment, the controller 740 does not need to calculate SpO$_2$ based on transmitted light received by the optical detector 730. For example, the controller 740 may calculate SpO$_2$ based on reflected light received by the optical detector 730.

Figure 10:
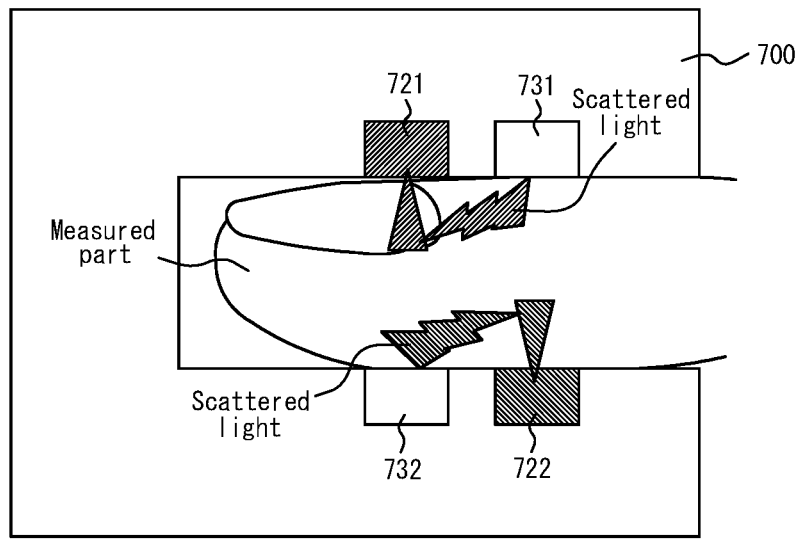
FIG. 10 is a schematic diagram illustrating another example of the using state of the measuring apparatus of FIG. 8.

FIG. 10 is a schematic diagram illustrating an example of another using state of the measuring apparatus 700, in which SpO$_2$ is calculated based on reflected light. In this example, the first optical detector 731 receives reflected light of laser light (red light) emitted by the first light source 721 from the measured part. In this example, the second optical detector 732 receives reflected light of laser light (near infrared light) emitted by the second light source 722 from the measured part.

In the example illustrated in FIG. 10, the first optical detector 731 is arranged in the measuring apparatus 700 on the same side with respect to the finger serving as the measured part. In the example illustrated in FIG. 10, the second optical detector 732 is arranged in the measuring apparatus 700 on the same side with respect to the finger serving as the measured part. As illustrated in FIG. 10, for example, both the first light source 721 and the first optical detector 731 are arranged to face the nail side of the finger. As illustrated in FIG. 10, for example, both the second light source 722 and the second optical detector 732 are arranged to face the pad side of the finger.

In this case, the controller 740 can calculate SpO$_2$ of the measured part based on outputs (i.e., photoelectric conversion light of reflected light) of the first optical detector 731 and the second optical detector 732. For example, the controller 740 calculates the ratio of the oxyhemoglobin to the reduced hemoglobin in the blood based on the intensity of the light received by the first optical detector 731 with respect to an amount of the light of the first wavelength emitted by the first light source 721 and the intensity of the light received by the second optical detector 732 with respect to an amount of the light of the second wavelength emitted by the second light source 722. Then, the controller 740 can calculate $SpO_2$ by using the following formula: $\{HbO_2/(Hb+HbO_2)\} \times 100$ based on the ratio of the oxyhemoglobin to the reduced hemoglobin. In the formula, for example, $HbO_2$ may be calculated based on the intensity of reflected light received by the first optical detector 731 after reflected by the oxyhemoglobin. In the formula, for example, $Hb+HbO_2$ may be calculated based on the intensity of reflected light received by the second optical detector 732 after reflected by the oxyhemoglobin and the reduced hemoglobin.

As described above, the controller 740 can calculate $SpO_2$ by using reflected light in place of transmitted light. When calculating $SpO_2$ by using reflected light, the controller 740 can calculate the blood flow amount as well based on the output of the second optical detector 732 by employing the blood flow amount measuring technology utilizing the Doppler shift as described in the first embodiment.

Fifth Embodiment

Figure 11:
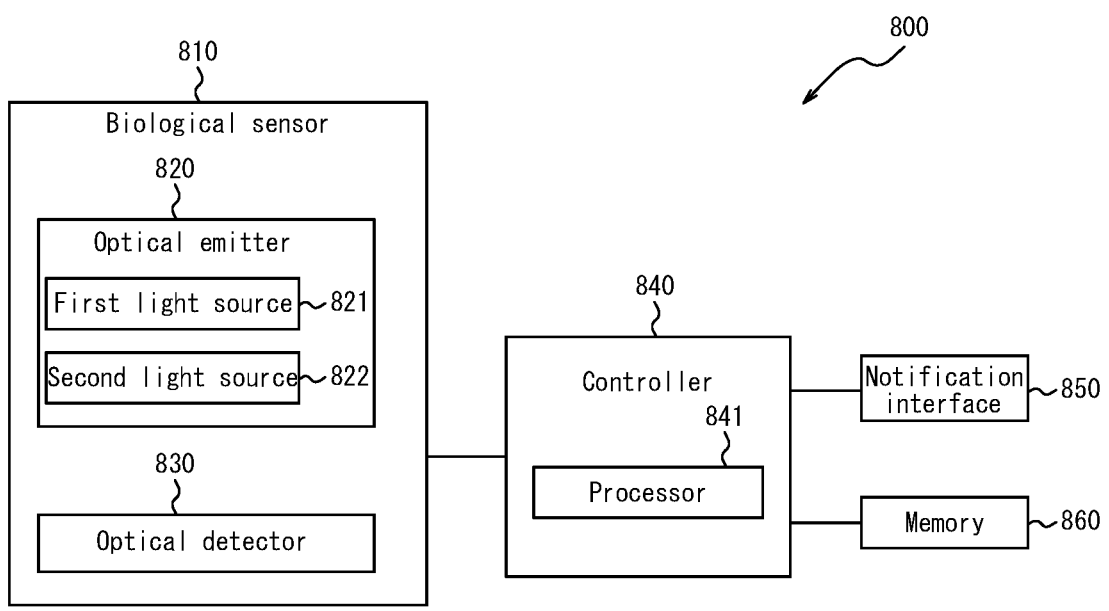
FIG. 11 is a functional block diagram illustrating a schematic configuration of a measuring apparatus according to a fifth embodiment.

FIG. 11 is a functional block diagram illustrating a schematic configuration of a measuring apparatus 800 according to a fifth embodiment. The measuring apparatus 800 includes a biological sensor 810, a controller 840, a notification interface 850, and a memory 860. The biological sensor 810 includes an optical emitter 820 and an optical detector 830.

The optical emitter 820 includes a first light source 821 and a second light source 822. The configuration and the function of the optical emitter 820 may be similar to those of the optical emitter 720 of the measuring apparatus 700 of the fourth embodiment. According to the present embodiment, however, the first light source 821 and the second light source 822 emit measuring light at different timings. For example, the first light source 821 and the second light source 822 alternately emit the measuring light at predetermined intervals.

The measuring apparatus 800 according to the present embodiment includes the optical detector 830 alone, unlike the measuring apparatus 700 of the fourth embodiment that includes two optical detectors. The optical detector 830 receives, for example, transmitted light of laser light (red light) emitted by the first light source 821 from the measured part. The optical detector 830 receives, for example, reflected light of laser light (near infrared light) emitted by the second light source 822 from the measured part. The optical detector 830 is configured as, for example, a multi-frequency-responsive PD. When laser light from the first light source 821 is emitted to the measured part, the optical detector 830 detects transmitted light from the measured part. When laser light from the second light source 822 is emitted to the measured part, the optical detector 830 receives reflected light from the measured part. The biological sensor 810 transmits a photoelectric conversion signal of the detection light received by the optical detector 830.

Figure 12:
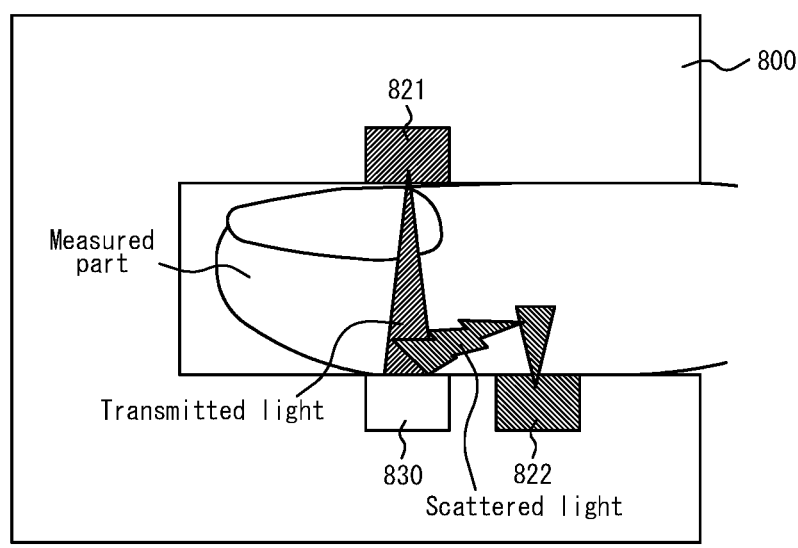
FIG. 12 is a schematic diagram illustrating an example of a using state of the measuring apparatus of FIG. 11.

FIG. 12 is a schematic diagram illustrating an example of a using state of the measuring apparatus 800. FIG. 12 is a diagram illustrating an example of a cross-section of the measuring apparatus 800 and the measured part. FIG. 12 illustrates the light sources of the optical emitter 820 and the optical detector 830 alone as the functional units of the measuring apparatus 800.

The optical detector 830 is arranged at a position of the measuring apparatus 800 opposing the first light source 821 across the finger serving as the measured part at the time of measurement of the biological information. The optical detector 830 is arranged on the same side of the measuring apparatus 800 with respect to the finger serving as the measured part. As illustrated in FIG. 12, for example, when the first light source 821 is arranged to face the nail side of the finger, the optical detector 830 and the second light source 822 are arranged to face the pad side of the finger. In this way, the optical detector 830 can detect transmitted light of the measuring light emitted by the first light source 821 and reflected light of the measuring light emitted by the second light source 822.

Referring back to FIG. 11, the controller 840 includes at least one processor 841 configured to control and manage the measuring apparatus 800 in its entirety including each functional block thereof. The functions of the controller 840 and the processor 841 may be similar to those of the controller 140 and the processor 141, respectively, of the first embodiment.

According to the present embodiment, the controller 840 calculates $SpO_2$ of the measured part based on outputs of the first optical detector 831 and the second optical detector 832 (i.e., the photoelectric conversion signals of transmitted light and reflected light). The controller 840 can calculate $SpO_2$ by employing the same principle as that described in the first embodiment. That is, the controller 840 calculates the ratio of the oxyhemoglobin to the reduced hemoglobin in the blood based on the intensity of transmitted light received by the optical detector 830 with respect to an amount of the light of the first wavelength emitted by the first light source 821 and the intensity of reflected light received by the optical detector 830 with respect to an amount of the light of the second wavelength emitted by the second light source 822. Then, the controller 840 calculates $SpO_2$ using the following formula: $\{HbO_2/(Hb+HbO_2)\} \times 100$ based on the ratio of the oxyhemoglobin to the reduced hemoglobin. In the formula, for example, $HbO_2$ may be calculated based on the intensity of transmitted light received by the optical detector 830 after a portion of the measuring light is absorbed by the reduced hemoglobin. In the formula, for example, $Hb+HbO_2$ may be calculated based on the intensity of reflected light received by the optical detector 830 reflected by the oxyhemoglobin and the reduced hemoglobin.

The functions of the notification interface 850 and the memory 860 are similar to those of the notification interface 150 and the memory 160, respectively, of the first embodiment. Thus, detailed descriptions will be omitted here.

The measuring apparatus 800 according to the present embodiment also can calculate $SpO_2$. The measuring apparatus 800 uses reflected light to calculate $SpO_2$. Thus, the measuring apparatus 800 can also calculate the blood flow amount based on the output of the optical detector 830 based on reflected light of the measuring light emitted by the second light source 822, by employing the blood flow amount measuring technology utilizing Doppler shift.

According to the present embodiment, the optical detector 830 has been described as receiving transmitted light of laser light (red light) emitted by the first light source 821 and reflected light of laser light (near infrared light) emitted by the second light source 822 from the measured part. However, the optical detector 830 may receive reflected light of laser light (red light) emitted by the first light source 821 and transmitted light of laser light (near infrared light) emitted by the second light source 822 from the measured part. In this case, the first light source 821 is arranged on the same side as the optical detector 830 with respect to the finger serving as the measured part, and the second light source 822 is arranged in a position opposing the optical detector 830 across the finger serving as the measured part. In this case also, the controller 840 can calculate $SpO_2$ by employing the same principle as that described in the first embodiment. In this case, however, in the formula described above, $HbO_2$ may be calculated based on the intensity of light reflected by the oxyhemoglobin and received by the optical detector 830, and $Hb+HbO_2$ may be calculated based on the intensity of transmitted light that is not absorbed by any one of the oxyhemoglobin and the reduced hemoglobin and received by the optical detector 830.

Although the measuring apparatus 800 according to the present embodiment has been described as including the optical detector 830 alone, the measuring apparatus 800 may include two optical detectors. In this case, one of the optical detectors may receive transmitted light of laser light emitted by the first light source 821 from the measured part, and the other may receive reflected light of laser light emitted by the second light source 822 from the measured part.

Some embodiments have been described in order to fully and clearly disclose the present disclosure. However, the appended claims are not limited to the above embodiments and can realize all example modifications and alternative configurations that can be created by those skilled in the art within the scope of the fundamentals shown herein. Each condition of the embodiments may be combined in any appropriate manner.

The measuring apparatuses (the measuring apparatuses 100, 200, and 400) described in the above embodiments can be mounted in various devices.

The controller of each of the embodiments has been described as estimating the likelihood that the subject gets altitude sickness based on the blood flow amount and $SpO_2$. However, the controller of each of the embodiments may detect a blood pressure, a dehydration state, a relaxed state, an autonomic state, or other symptoms such as a heart disease, based on at least one of the blood flow amount and $SpO_2$.

The invention claimed is:

1. A measuring apparatus comprising:
   a first light source for emitting light of a first wavelength;
   a second light source for emitting laser light of a second wavelength different from the first wavelength;
   a first optical detector for receiving scattered laser light of the second wavelength from a light irradiated part;
   a second optical detector for receiving transmitted light of the first wavelength from the light irradiated part;
   a third optical detector for receiving transmitted laser light of the second wavelength from the light irradiated part; and
   a controller configured to measure a blood flow amount based on an output of the first optical detector and an oxygen saturation based on outputs of the second optical detector and the third optical detector,
   wherein the second optical detector and third optical detector are arranged on an opposite side of the first light source and the second light source with respect to the light irradiated part and the first optical detector is arranged on a same side of the first light source and the second light source with respect to the light irradiated part.

2. The measuring apparatus according to claim 1, wherein the first light source for emitting the light of the first wavelength is an LED light source or a laser light source for emitting the light of the first wavelength.

3. The measuring apparatus according to claim 1, wherein the light of the first wavelength is a red light, and the laser light of the second wavelength is a near infrared light.

4. The measuring apparatus according to claim 1, wherein the controller estimates a likelihood that a subject gets altitude sickness based on the oxygen saturation and the blood flow amount.

5. A measuring method of a measuring apparatus comprising:
   a step of emitting light of a first wavelength to a light irradiated part;
   a step of emitting laser light of a second wavelength different from the first wavelength to the light irradiated part;
   a step of receiving scattered laser light of the second wavelength from the light irradiated part;
   a step of receiving transmitted light of the first wavelength from the light irradiated part at a first location;
   a step of receiving transmitted laser light of the second wavelength from the light irradiated part at a second location, the second location being different than the first location;
   a step of measuring a blood flow amount based on the scattered laser light of the second wavelength; and
   a step of measuring an oxygen saturation based on the transmitted light of the first wavelength and the transmitted laser light of the second wavelength,
   wherein the step of receiving transmitted light of the first wavelength and the step of receiving transmitted laser light of the second wavelength are performed on an opposite side of the step of emitting light of the first wavelength and the step of emitting laser light of the second wavelength with respect to the light irradiated part and the step of receiving scattered laser light is performed on a same side of the step of emitting light of the first wavelength and the step of emitting laser light of the second wavelength with respect to the light irradiated part.

6. A measuring apparatus comprising:
   a first light source for emitting laser light of a first wavelength;
   a second light source for emitting laser light of a second wavelength different from the first wavelength;
   a first optical detector for receiving transmitted laser light of the first wavelength from a light irradiated part;
   a second optical detector for receiving transmitted laser light of the second wavelength and scattered laser light of the first wavelength from the light irradiated part; and
   a controller configured to measure a blood flow amount and an oxygen saturation based on outputs of the first optical detector and the second optical detector.

7. A measuring method of a measuring apparatus comprising:
   a step of emitting laser light of a first wavelength to a light irradiated part;
   a step of emitting laser light of a second wavelength different from the first wavelength to the light irradiated part;
   a step of receiving transmitted laser light of the first wavelength from the light irradiated part;
   a step of receiving transmitted laser light of the second wavelength and scattered laser light of the first wavelength from the light irradiated part; and
   a step of measuring a blood flow amount and an oxygen saturation based on the transmitted laser light of the first wavelength, the transmitted laser light of the second wavelength, and the scattered laser light of the first wavelength.

\* \* \* \* \*